United States Patent [19]

Schreiber

[11] Patent Number: 4,639,532
[45] Date of Patent: Jan. 27, 1987

[54] PROCESS FOR PREPARING SYNTHETIC PERIPLANONE-B

[75] Inventor: Stuart L. Schreiber, Bethany, Conn.

[73] Assignee: Yale University, New Haven, Conn.

[21] Appl. No.: 621,574

[22] Filed: Jun. 18, 1984

[51] Int. Cl.[4] .......................................... C07D 493/10
[52] U.S. Cl. .................................. 549/332; 549/546; 568/42; 568/374; 568/375; 568/819
[58] Field of Search ......................................... 549/332

[56] References Cited

U.S. PATENT DOCUMENTS 4,339,388  7/1982  Still ..................................... 549/332

OTHER PUBLICATIONS

Stuart L. Schreiber et al, Tetrahedron Letters, vol. 22(46) (1981), pp. 4651–4654.
W. Clark Still, Jour. Am. Chem. Soc., vol. 101:9, Apr. 25, 1979, pp. 2493–2495.
Michael A. Adams et al, Jour. Am. Chem. Soc., vol. 101:9, Apr. 25, 1979.
Stuart L. Schreiber et al, Jour. Am. Chem. Soc., vol. 106 (1984), pp. 4038–4039.

*Primary Examiner*—Norma S. Milestone
*Attorney, Agent, or Firm*—Ostrolenk, Faber, Gerb & Soffen

[57] ABSTRACT

Disclosed is an improved process for synthesizing periplanone-B, the sex attractant and sex excitant pheromone of the American cockroach, *Periplaneta americana*.

8 Claims, No Drawings

PROCESS FOR PREPARING SYNTHETIC PERIPLANONE-B

BACKGROUND OF THE INVENTION

1. Field of the Invention

The present invention relates to a process for preparing synthetic periplanone-B, the sex attractant and sex excitant pheromone of the American cockroach, *Periplaneta americana*.

2. Description of the Prior Art

Females of the species *Periplaneta americana*, the American cockroach, have long been known to produce an extraordinarily potent sex pheromone. Unfortunately, isolation and structural characterization of this pheromone were hampered due to the fact that the phermone is stored only in minute quantities ($<<1$ μg) by individual cockroaches. Eventually, however, through a massive cockroach rearing and extraction program utilizing more than 75,000 virgin female cockroaches, C. J. Persoons, et al. were able to isolate two compounds, periplanone-A and periplanone-B. The major component was periplanone-B, which was found to be extremely active as a sex pheromone.

Subsequent structural studies of periplanone-B revealed that periplanone-B has the structure:

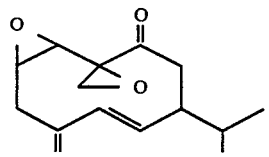

However, the complete stereochemistry of the compound was not known until the work of W. C. Still et al. which revealed the compound to have the following structure:

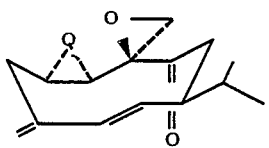

This structure may also be drawn as follows:

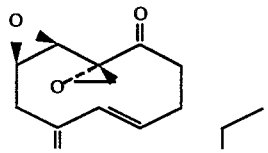

Since periplanone-B is such a strong sex attractant for the American cockroach, it would be highly desirable to incorporate it in, for example, compositions containing an insecticide effective against cockroaches. The male American cockroach would thus be attracted to the insecticide and killed by it. However, as noted above, it is virtually impossible to isolate natural periplanone-B from female cockroachhes in the quantities which would be required for use in commercial insecticides. Thus, a method for synthesizing periplanone-B was sought.

During their studies into the stereochemistry of periplanone-B Still et al. were successful in synthesizing periplanone-B via a process requiring about twenty-four steps. Since it is always desirable to simplify a synthesis or make it more efficient, improvements on the Still et al. technique were sought. The desired improved synthesis would provide a method for preparing periplanone-B relatively easily in quantities sufficient to make the compound available commercially.

A new synthesis for periplanone-B has now been discovered which requires only about one half the number of steps as the Still et al. process, and which makes it possible to prepare periplanone-B synthetically in commercial quantities.

SUMMARY OF THE INVENTION

In accordance with the present invention there is provided a process for synthesizing periplanone-B comprising:

a. reacting allene and 4-isopropyl-2-cyclohexen-1-one by photocycloaddition to form a mixture of

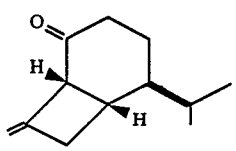

and

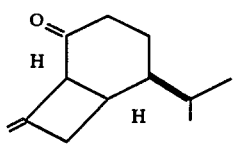

in a molar ratio of anti (IIIa) to syn (IIIb) isomers of about 2/1;

b. reacting the mixture of IIIa and IIIb with a vinyl anion reagent to form the corresponding allylic carbinols having the structure

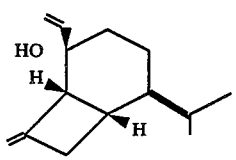

and

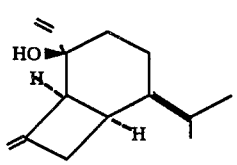

in a molar ratio of anti to syn isomers of about 2/1;

c. reacting the product of step b by anion-accelerated oxy-Cope rearrangement to form compounds having the structure

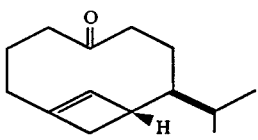

and

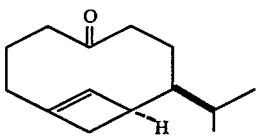

in a molar ratio of cyclobutene isomers of about 2/1;

d. reacting the product of step c by electrocyclic ring opening to form a mixture of

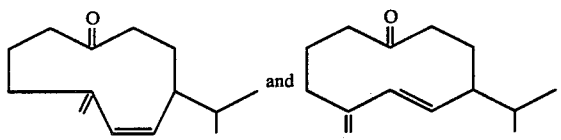

in a molar ratio of cis-diene (VI) to trans-diene (VII) of about 2/1;

e. photoisomerizing the mixture produced in step d to form a mixture of VI and VII in a molar ratio of 1/15, respectively, and isolating VII from such mixture;

f. enolizing VII with a base strong enough to deprotonate a ketone followed by sulfenylation to form a 16/1 regioisomeric mixture of monosulfenylated ketones having the general formula:

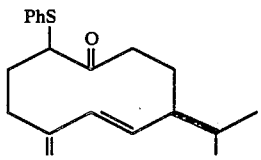

g. oxidizing the product of step f to form the corresponding sulfoxides followed by pyrolysis to form

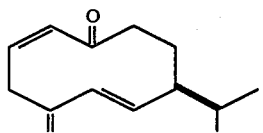

and isolating IX from the reaction mixture;

h. stereoselectively epoxidizing IX to form a mixture of cis epoxides in a molar ratio of beta/alpha of about 4/1

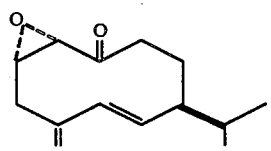

alpha-epoxide

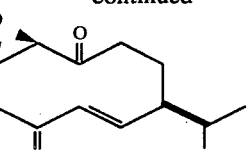

beta-epoxide i. selenylizing Xa and Xb to form the selenide

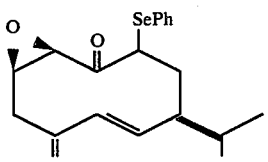

oxidizing XI to the corresponding selenoxide and rearranging the selenoxide by Selena-Pummerer rearrangement to form the alpha-diketone

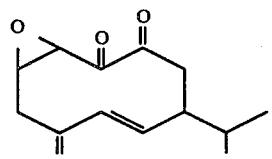

j. mono-epoxidizing XII to form periplanone-B having the structure

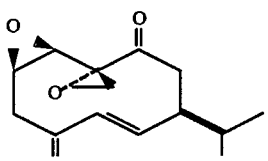

There are also provided in accordance with the present invention the aforementioned compounds IIIa, IIIb, IVa, IVb, Va, Vb, VII, VII, VIII, IX, Xa, Xb, XI and XII. These compounds are useful as chemical intermediates in the synthesis of periplanone-B or as chemical intermediates for the preparation of a compound which is in turn a chemical intermiediate useful for synthesizing periplanone-B.

DETAILED DESCRIPTION OF THE PREFERRED EMBODIMENTS

The individual steps a–j of the process of this invention may be performed using a variety of reaction conditions (e.g. solvent, reaction temperature, reaction time, etc.). Typical reaction conditions for each of steps a–j are provided in the following Example, but these specific reaction conditions are not intended to limit the invention in any manner. Reaction solvents, reaction temperatures and reaction times given in the Example may, thus, be varied and still remain with the scope of the invention although varying such reaction conditions may, of course, cause a change in reaction rate, yield or the like.

In step b of the process of the present invention, compounds IIIa and IIIb are reacted with a vinyl anion reagent to form allylic carbinols. The vinyl anion reagents useful in this step of the process are compounds having a vinyl anion and a metal cation. One example of such vinyl anion reagents is vinyl magnesium bromide, although other vinyl metallic halides would be useful as well and should be considered equivalent to vinyl magnesium bromide.

Step c of the present process involves an oxy-Cope rearrangement to form compounds Va and Vb. In general, a strong base which will deprotonate in alcohol is employed in this step, one example of which is the combination of 18-Crown-6 and KH.

The enolization of compound VII in step f can be accomplished with a base strong enough to deprotonate a ketone. Preferably, the base is a strong amide base such as lithium hexamethyldisilazide.

The sulfenylation in step f may be accomplished with Trost's sulfenylating agent, i.e., benzenesulfonate-S-phenyl ester (PhSSO$_2$PPh), although other sulfenylating agents may be employed with substantially equivalent results.

Oxidation of the product of step f may be accomplished by a strong oxidizing agent such as, for example, NaIO$_4$.

With respect to the alpha and beta epoxides produced in step h, it has been quite unexpectedly found that it is not necessary to separate the alpha and beta products even though the beta form is the desired product and the mixture contains about 20% alpha epoxide. The alpha/beta mixture can be employed as such in step i with the result being a good yield of the desired product XII without any apparent adverse effect from the presence of the alpha epoxide in the reaction mixture.

EXAMPLE

A 250 ml. pyrex photochemical reactor (Ace Glass Inc.), into which a magnetic stirring bar had been placed, was fitted with a quartz immersion well. The reactor was clamped so that it would rest inside a black rubber 1 gal. safety carrier (Fisher Scientific Products), which in turn sat atop a magnetic stir plate. The smallest side arm of the reactor was fitted with a rubber septum through which which a 20 gauge Teflon tube, long enough to reach the bottom of the reactor, had been passed. The next smallest side arm was fitted with a rubber septum. The largest side arm was fitted with a dry ice condenser.

Cooling for the outside of the reactor was accomplished by filling the black rubber safety carrier with isopropanol up to the level just below the smallest side arm, and by immersing into the isopropanol the cooling wand of a cryogenic cooler (Neslab Instruments Inc., Model CC-100). The cooler was set so as to keep the isopropanol at $-35°$ C.

Cooling for the immersion well was accomplished by using a submersible pump (Little Giant Model 1) in 1.5 gal. of methanol to pump methanol through cooling coils, into the immersion well, and back out to the pump. The cooling coils were submerged in 3 gal. of acetone which was placed in a 5 gal. Dewar flask. The acetone was maintained at $-50°$ by the addition of dry ice.

The apparatus described above was set up, but no cooling was started until the substrate was placed in the reactor. Thus, 10.6 g. of 4-isopropyl-2-cyclohexen-1-one was placed in the reactor at 25° C. and diluted with 200 ml. of dry, freshly distilled ethyl ether. The solution was vigorously stirred, and a slow stream of dry nitrogen gas was continuously passed through the Teflon tube and the solution throughout the entire course of the reaction. All ground glass joints and rubber septa were sealed with Parafilm to prevent the escape of allene. With the substrate in the reactor, cooling was begun. Thus, the cryogenic apparatus was turned on, the methanol was circulated through the immersion well at $-50°$ C., and the dry ice condenser was filled with dry ice/isopropanol. During the interval required to cool down the apparatus to $-30°$ C., a Pyrex filter was lowered into the immersion well. Once the isopropanol surrounding the reactor had reached $-30°$ C., gaseous allene was passed into the reactor through a large gauge syringe needle which pierced the rubber septum on the second smallest side arm. Allene was passed in until the level of the solution in the reactor had risen to just below the smallest side arm (about 35 ml.).

With all the reactants inside the apparatus, the top of the black rubber safety carrier and the photochemical reactor were wrapped with aluminum foil to prevent the escape of stray light. A 450-W. Hanovia medium pressure mercury lamp was turned on outside the apparatus and slowly lowered into the immersion well so that it sat just above the bottom of the well, not touching it.

The solution was irradiated for 25 hours with stirring and cooling. At the end of this time, the lamp was shut off and withdrawn from the immersion well. The cryogenic apparatus was also shut off, and the cooling coils were withdrawn from the acetone bath. Methanol circulation was continued until the apparatus had reached room temperature. Upon reaching room temperature, methanol circulation was stopped, and the cooling coils disconnected. The dry ice condenser and Teflon tube were removed, and the photochemical reactor was lifted from the isopropanol bath. The solution was recovered, concentrated in vacuo and placed atop a column of silica gel (Merck Silica Gel 60, 25×3 cm). The material was eluted with 600 ml. 5:1 hexane/ethyl acetate, with all the eluant being collected in a 1-liter r.b. flask.

The eluant was concentrated in vacuo, yielding 9.9 g. (72%) of partially purified photoadducts IIIa and IIIb in a 2:1 ratio.

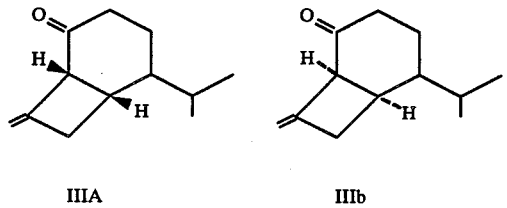

IIIA            IIIb

A dry, 1-liter 3-neck flask was fitted with a mechanical stirrer in the center neck and a 250 ml. dropping funnel in one side arm. The flask was clamped so that it sat inside a styrofoam ice bucket.

In the flask was placed 167 ml. of 1M vinylmagnesium bromide in THF (Aldrich; 3 equivalents) via syringe. 200 ml. of dry, freshly distilled ethyl ether were added via canula. In the dropping funnel were placed 9.9 g. of the photoadducts IIIa and IIIb dissolved in 125 ml. dry ethyl ether.

The flask was cooled to $-70°$ C. with dry ice/isopropanol under N$_2$, and the contents of the dropping funnel were added dropwise to the flask over the course of one hour. After addition was complete, the dropping funnel was rinsed down with two 25 ml. portions of ethyl ether via syringe. The reaction was quenched at −70° C. with 50 ml. sat. aq. NH4Cl, and then allowed to come to room temperature.

The reaction mixture was washed into a 2-liter separatory funnel with two 100 ml. portions of ether, and then another 400 ml. of ether were added.

The aqueous layer was drawn off, and the organic layer was washed with twice with 30 ml. of brine. The washing were back-extracted with twice with 50 ml. ether. The combined organic layers were dried over MgSO4, then filtered and concentrated in vacuo.

The residue was chromatographed on silica gel with 10:1 hexane/ethyl acetate (25×3 cm.). Although the disastereomeric allylic alcohols IVa and IVb were readily separable, no attempt to collect them separately was made.

From this was isolated 7.242 g. allylic alcohols IIVa and IVb in a 2:1 ratio (63%).

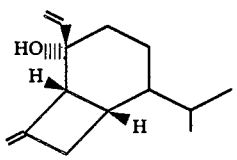
IVa

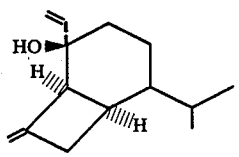
IVb

A dry, tared 500 ml. r.b. flask was placed inside a nitrogen-purged glove bag (Aldrich Atmosbag). Within the nitrogen atmosphere, 46.5 g. dry 18-Crown-6 were transferred to the flask (Aldrich: 5 equivalents).

The stopped flask was withdrawn from the nitrogen bag, and equipped with a stir bar and a reflux condenser. To the flask were added 7.23 g. allylic alcohols IVa and IVb dissolved in 250 ml. dry, freshly distilled THF.

In a dry, 100 ml. pear shaped flask containing a stir bar were placed about 6 g. 35% KH mineral oil dispersion (Aldrich). The reagent was rendered oil-free by five sequential washings with pentane (15 ml. each). The dispersion was vigorously stirred with pentane each time and allowed to settle to the bottom. The supernatant was then drawn off by syringe under N2.

After the fifth washing, excess pentane was blown off with N2 until the KH was dry. 15 ml. dry THF were added via syringe, and the slurry was mixed thoroughly.

With vigorous stirring the KH slurry was added via pipette in approximately 0.5 ml. portions to the solution containing IVa and IVb. Instantly, gas evolution was observed, and the color of the solution went from yellow to orange to dark brown as deprotonation progressed. Addition of KH continued in 1 minute intervals until the solution had become opaque and excess KH could be seen on the bottom if stirring was interrupted.

The solution was refluxed for 30 minutes. The now black solution was cooled to 0° C. and carefully quenched by adding sat. aq. NH4Cl through the top of the condenser.

The solution was washed into a 2-liter separatory funnel with 1 liter of ethyl ether. The aqueous layer was drawn off, and the organic layer was washed with sat. aq. NaHCO3 until the aqueous layers were clear. This procedure was found to be the most effective in removing excess 18-Crown-6. The aqueous layers were back-washed once with ether, and the combined organic solutions were dried over MgSO4. Filtration, removal of solvents and chromatography over silica gel with 10:1 hexane/ethyl acetate (20×3 cm) gave 5.41 g. of a 2:1 mixture of cyclobutene bridgehead olefins Va and Vb (75%).

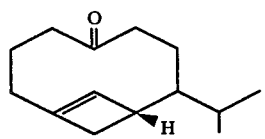
Va

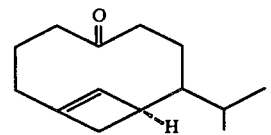
Vb

In a 250 ml. general purpose bomb reactor were placed in two separate batches, 5.40 g. of cyclobutenes Va and Vb which were dissolved in 400 ml. of dry toluene.

The solutions were heated at 175° C. for 20 hours. After heating, each batch was washed into a 500 ml. round bottom flask with hexane and concentrated in vacuo. The combined batches were placed atop a silica gel column (20×2 cm) and eluted with 500 ml. of 10:1 hexane/ethyl acetate into a 1 liter round bottom flask. From this was obtained 4.18 g. of a 2:1 mixture of cis diene VI trans diene VII (77%).

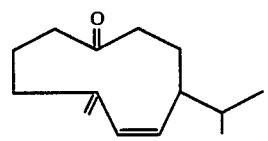
VI

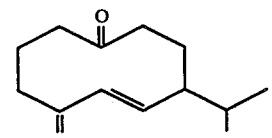
VII

A 250 ml. pyrex photochemical reactor (Ace Glass Inc.), into which a magnetic stirring bar had been placed, was fitted with a quartz immersion well. The two smallest sidearms were sealed with rubber septa, while the largest sidearm was fitted with a water cooled condenser. The reactor was clamped so that it sat atop a stir plate, and was wrapped in aluminun foil to prevent the escape of stray light. Cooling for the immersion well was provided by the circulation of cold water. 4.17 g. of the 2:1 mixture of dienes VI and VII were placed in the reactor and diluted with 200 ml. of dry, freshly distilled benzene.

A Vycor filter was placed in the immersion well, and the solution was irradiated with a 450-W Hanovia medium pressure mercury lamp for 5 hours with stirring.

At the end of this time, the lamp was shut off and removed from the immersion well. The water cooled condenser was also removed, and the immersion well was lifted out of the reactor while being washed down with hexane to remove any solution clinging to the well. The solution was washed out of the reactor with hexane into a 500 ml. round bottom flask and concentrated in vacuo.

The residue was placed atop a silica gel column and chromatographed with 10:1 hexane/ethyl acetage (20×2 cm.). From this was isolated 0.214 g. of cis diene VI and 3.205 g. of trans diene VII (5% and 77% respectively).

A dry 50 ml. round bottom flask, into which a magnetic stirring bar had been placed, was fitted with a rubber septum and nitrogen inlet. The flask was cooled to −10° C. with an ice/methanol bath. 20 ml. of dry, freshly distilled THF were added via syringe, followed by 0.907 ml. of dry, distilled NH(Me₃Si)₂ (4.29 mmol; 1.25 equivalents). To this solution was added dropwise via syringe 1.89 ml. of 2.27M n-butyllithium (4.29 mmol; 1.25 equivalents.)

After stirring for 5 minutes, the ice/methanol bath was removed and immediately replaced with a dry ice/isopropanol bath (−75° C.). To the flask was then added, dropwise via syringe, 0.706 g. of trans diene VII which was dissolved in 10 ml. of dry THF. The solution was stirred for 1 hour, during which the color became a pale but distinct yellow.

During the time that the enolization was progressing, 1.748 g. of Trost's sulfenylating reagent, benzenesulfonate-S-phenyl ester (PhSSO₂Ph), was weighed in a 15 ml. dry round bottom flask containing a magnetic stirring bar. To this reagent were added 5 ml. of dry THF, and the solution was stirred until all the solid had dissolved.

At the end of 1 hour, 2.70 ml. of the solution of PhSSO₂Ph prepared as described (0.944 g.; 3.77 mmol; 1.1 equivalents) were added via syringe over the course of 30 seconds to the 50 ml. flask.

The solution was stirred for 10 minutes after addition of the sulfenylating reagent was complete, at which time 1 ml. of sat. aq. NH₄Cl was added to the solution via syringe. The dry ice/isopropanol bath was removed and the solution allowed to warm to room temperature. The solution was then transferred to a 250 ml. separatory funnel and diluted with 150 ml. of ethyl ether. The aqueous layer was drawn off and the etherial layer was washed twice with 1 ml. portions of sat. aq. NaHCO₃, followed by 2 ml. of brine. The etherial layer was dried over MgSO₄, filtered and concentrated in vacuo.

NMR analysis (250 MHz) of the residue after removal of all volatiles indicated a 16:1 mixture of phenylsulfenylated ketone VIII and it's regioisomeric C-9 counterpart.

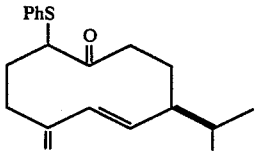

VIII

The residue from sulfenylation was transferred to a 500 ml. round bottom flask having a magnetic stirring bar and dissolved in 300 ml. of anhydrous methanol. To this stirred solution was added 11.0 g. of NaIO₄ in 125 ml. of water (51.5 mmol; 15 equivalents). The cloudy solution was stirred at room temperature for 14 hours, during which a solid precipitated from solution.

At the end of this time, the solution was filtered free of solid and concentrated in vacuo. During concentration, more white solid precipitated from the solution. After methanol and water had been removed, the mixture of solid and organic material was washed out of the flask with chloroform and once again filtered free of solids. Removal of chloroform in vacuo left a yellow residue which was placed atop a silica gel column (15×1 cm.) and chromatographed with 4:1 hexane/ethyl acetate. From this was isolated 0.802 g. of 1:1 mixture of C-1 sulfoxide diastereomers contaminated with the corresponding C-9 sulfoxide diastereomers (71%). (C-1/C-9 sulfoxides=16/1).

A 100 ml. round bottom flask was equipped with magnetic stirring bar and a reflux condenser. Into the flask was placed 0.619 g. of the sulfoxides derived predominantly from phenylsulfenylated ketone VIII. The sulfoxides were diluted with 50 ml. of dry toluene and stirred with approx. 0.75 g. of CaCO₃. The solution was heated in a 110° C. oil bath with stirring under nitrogen for 12 hours.

At the end of this time, the now distinctively yellow solution was filtered free of solids using benzene to wash down the solution. Removal of solvents in vacuo left a yellow residue which was placed atop a column of silica gel (12×1 cm.) and eluted with 15:1 hexane/ethyl acetate.

From this was isolated 0.172 g. of enone IX (45%) as a very pale greenish oil with a characteristically sharp and disagreeable odor.

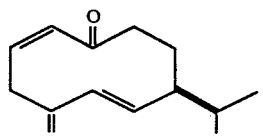

IX

A dry 25 ml. round bottom flask containing a magnetic stirring bar was fitted with a loose rubber septum. 0.172 g. of enone IX was placed in the flask and dissolved in 5 ml. of dry THF. To this solution was added, via pipette, 2 ml. of 90% tert-butyl hydroperoxide (Aldrich).

In a separate, dry, 25 ml. pear shaped flask containing a magnetic stirring bar, there was placed approx. 0.5 g. of 35% KH mineral oil dispersion (Aldrich). The KH was rendered oil free by five sequential pentane washings (5 ml. each). The dispersion was vigorously stirred with pentane each time and allowed to settle to the bottom. The supernatant was then drawn off with a pipette.

After the fifth wash, the excess pentane was blown off with N₂, and 5 ml. of dry THF were added to the KH. The mixture was stirred vigorously until it became a slurry.

The flask containing the enone IX was cooled at 0° C. in an ice water bath. To this solution was added three drops of the KH/THF slurry. Immediate gas evolution was accompanied by a sizzling sound. The cloudy, heterogenous solution was allowed to warm to room temperature, where it became homogenous and pale green. The solution was stirred at room temperature for 1.5 hours.

At the end of this time, 5 rops of sat. aq. NH₄Cl were added via pipette, and the entire reaction mixture was transferred to a 60 ml. separatory funnel and diluted with 40 ml. of ethyl ether. The aqueous layer was separated, and the etherial layer was washed with one 1 ml. portion of brine. The organic layer was dried over MgSO₄, filtered and concentrated in vacuo (tert-butyl hydroperoxide was removed under high vacuum).

The residue was placed atop a silica gel column (10×1 cm) and eluted with 8:1 hexane/ethyl acetate. From this was recovered 0.154 g. of a 4:1 mixture (by NMR integration) of beta epoxy ketone Xb and it's alpha-epoxy diastereomer Xa (83%).

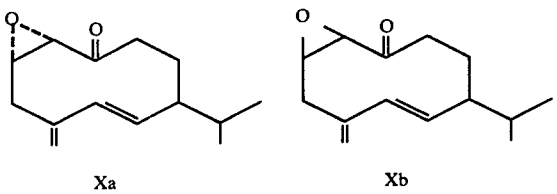

A dry, 15 ml. round bottom flask was equipped with a magnetic stirring bar and a rubber septum. The flask was cooled to −10° C. in an ice/methanol bath. To the flask was added 2 ml. of dry THF, followed by 47 μl. of HN(Me₃Si)₂ (0.221 mmol; 1.25 equivalents).

To this stirred solution was added, dropwise via syringe, 104 μl. of 2.13M n-butyllithium (0.221 mmol; 1.25 equivalents). After stirring for 5 minutes at −10° C., the ice/methanol bath was removed and immediately replaced with a dry ice/isopropanol bath (−75° C.). To the solution was added 39 mg. of the 4:1 mixture of beta epoxyketone Xb and it's alpha-epoxy diastereomer, Xa. The solution was stirred for 1 hour, during which time the solution acquired a pale yellow color.

During the time enolization was proceeding, a dry 5 ml. round bottom flask was equipped with a magnetic stirring bar and a rubber septum. Into this flask was weighed 111.7 mg of diphenyl diselenide (PhSe)₂. To the flask were added 2 ml. of dry THF under nitrogen, and the solution was stirred to room temperature until all the solid had dissolved. To the deep yellow solution were added 21.6 μl. of bromine. The solution fumed and immediately turned dark blood red.

At the end of 1 hour, 0.47 ml of the PhSeBr solution prepared above, (0.195 mmol; 1.1 equivalents) were added to the solution in the 15 ml. flask at −75° C. via syringe. After stirring for an additional 5 min., 0.5 ml. of sat. aq. NH₄Cl was added via syringe at −75° C. The dry ice/isopropanol bath was removed and the solution was allowed to warm to room temperature.

The reaction mixture was transferred to a 60 ml. separatory funnel and diluted with 30 ml. of ethyl ether. The aqueous layer was drawn off and the etherial layer was washed once with 0.5 ml. of brine. The ether layer was dried over MgSO₄, filtered and concentrated in vacuo. The residue was placed atop a silica gel column (6×0.5 cm.) and eluted with 10:1 hexane/ethyl acetate. From this was isolated 49 mg of a 10:1 mixture of phenylseleno epoxyketone XI and it's alpha-epoxy diastereomer (total yield=74%; yield of desired XI=83%).

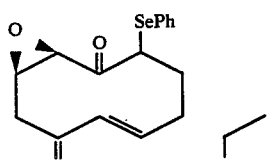

A 10 ml. round bottom flask was equipped with a stirring bar and a rubber septum. Into the flask was placed 26 mg. of phenylseleno epoxy ketone XI, followed by 1.5 ml. of THF and 1 ml. of aqueous 30% H₂O₂. The homogenous solution was stirred at room temperature for one hour, during which it lost its initial pale yellow color.

After this time, the solution was transferred to a 50 ml. round bottom flask containing a magnetic stirring bar and diluted with 25 ml. of distilled chloroform. The aqueous H₂O₂ separated from the organic phase, and was removed by stirring the chloroform solution over anhydrous K₂CO₃ for 15 min.

After 15 minutes, the solution was filtered free of solid and concentrated in vacuo. The residue was dissolved in 2 ml. of dry THF and stirred with 57 mg of anhydrous sodium acetate (0.69 mmol; 10 equivalents). To this mixture was added 33 μl. of acetic anhydride (distilled from P₂O₅) at room temperature (5 equivalents) The slightly yellow and cloudy mixture was stirred under nitrogen for 1.5 hours.

At the end of this time, the magnetic stirring bar was removed and approximately 1 ml. of the THF was removed in vacuo. The mixture was then diluted with 2 ml. anhydrous methanol and 50 mg. of anhydrous K₂CO₃ were added, followed by 3 drops of water. The mixture was stirred for an additional hour.

After 1 hour, the mixture was diluted with 20 ml. of chloroform, filtered free of solids, concentrated and placed atop a silica gel column (4×0.5 cm). The column was eluted with 20:1 hexane/ethyl acetate to provide 9.6 mg. of epoxy diketone XII (60%).

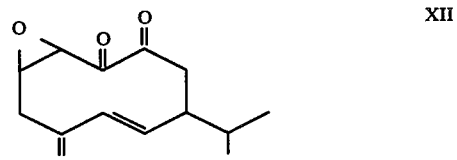

A dry, tared 25 ml. pear shaped flask was equipped with a magnetic stirring bar and a loose rubber septum with nitrogen inlet. Approximately 0.4 g. of 60% NaH in mineral oil (Aldrich) were placed in the flask. The reagent was washed free of oil by 5 consecutive pentane washings. The dispersion was vigorously stirred with pentane (5 ml.) each time and allowed to settle to the bottom. The supernatant was drawn off each time by syringe under nitrogen. After the fifth wash, excess pentane was blown off under a stream of nitrogen. Residual pentane was pumped off under high vacuum, with the vacuum being broken to dry nitrogen. In this manner, 136 mg. of NaH were purified.

To the flask was then added 6 ml. of dry, distilled DMSO. The flask was heated in a 70° O. oil bath for 45 minutes with vigorous stirring. After 45 minutes, with almost all the NaH consumed, stirring was stopped and the 0.94M solution of dimsyl sodium was allowed to cool to room temperature.

In another dry, tared 5 ml. round bottom flask, 154 mg. of trimethylsulfonium iodide were weighed. A magnetic stirring bar was added, followed by 1 ml. of dry, distilled DMSO. The solution was stirred under nitrogen until all the solid had dissolved.

Another 10 ml. dry round bottom flask was equipped with a magnetic stirring bar and rubber septum with a nitrogen inlet. The 10 ml. flask was cooled to −10° C. in an ice/methanol bath. There was placed in the flask 1 ml. of dry THF, followed by 120 μl. of the trimethylsulfonium iodide solution described above (0.091 mmol; 3 equivalents). To this solution was added 97 μl. of the dimsyl sodium solution described above (0.091 mmol; 3 equivalents). The solution immediately turned a cloudy yellow. The ylide was stirred for 2 minutes at −10° C. To this solution was added 7.1 mg. of diketone XII. The reaction was stirred for 10 minutes at −10° C., and then quenched with 0.5 ml. of sat. aq. NH₄Cl which was added via syringe.

The reaction mixture was diluted with 25 ml. of chloroform and stirred over MgSO₄ for 5 min., after which the solution was filtered and concentrated in vacuo. The residue was placed atop a silica gel column (4×0.5 cm.) and eluted with 10:1 hexane/ethyl acetate. From this was isolated 4.6 mg of ±periplanone-B I. (62% yield)

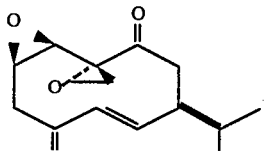
                                                                I

The structure of the product I was verified by NMR analysis (proton and $C^{13}$), MS, UV and IR.

In addition to I, 2.1 mg. of a more polar compound was recovered which was shown by NMR and GC/MS to be an isomer of periplanone-B (30% yield).

The periplanone-B produced by the above-described process was confirmed by bioassay to be an extremely potent sex excitant/attractant for the American cockroach, *Periplaneta americana*.

It should also be noted that the product of the above Example is a racemic mixture due to the fact that a racemic mixture was used for the starting materials. The racemic mixture produced was, as noted, highly active biologically. However, should it be desirable to produce a particular enantiomer of periplanone-B, this can be readily accomplished by practicing the process of this invention using starting materials of the desired enantiomeric form.

I claim:

1. A process for synthesizing periplanone-B comprising:

a. reacting allene and 4-isopropyl-2-cyclohexen-1-one by photocycloaddition to form a mixture of:

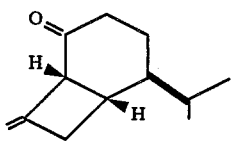
                                                              IIIa and

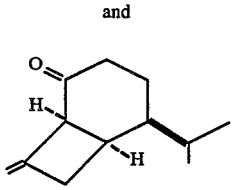
                                                              IIIb b. reacting the mixture of IIIa and IIIb with a vinyl metallic halide to form the corresponding allylic carbinols having the structure:

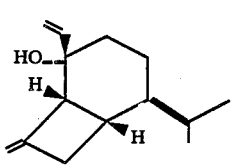
                                                              IVa and -continued

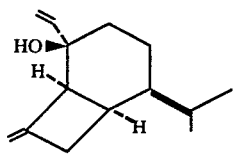
                                                              IVb c. reacting the product of step b with strong base which will deprotonate an alcohol to form compounds having the structure:

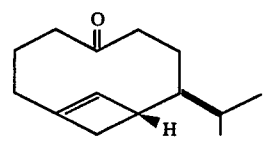
                                                              Va and

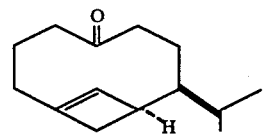
                                                              Vb d. heating the product of step c to thereby obtain electrocyclic ring opening to form a mixture of:

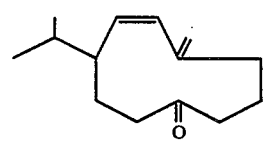
                                                              VI

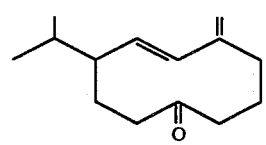
                                                              VII in a molar ratio of cis-diene (VI) to trans-diene (VII) of about 2/1;

e. irradiating with light the mixture produced in step d to form a mixture of VI and VII in a molar ratio of 1/15, respectively and isolating VII from such mixture;

f. reacting VII with a base strong enough to deproponate a ketone followed by reaction with a sulfenylating agent to form a 16/1 regioisomeric mixture of monosulfenylated ketones having the general formula:

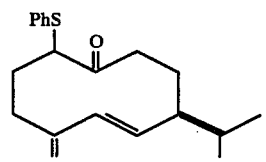
                                                              VIII g. reacting the product of step f with NaIO₄ to form the corresponding sulfoxides followed by pyrolysis to form:

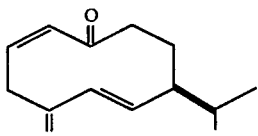

IX and isolating IX from the reaction mixture;

h. reacting IX with t-butyl hydroperoxide to form a mixture of cis epoxides Xa and Xb in a molar ratio of beta/alpha of about 4/1

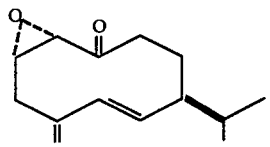

Xa alpha-epoxide

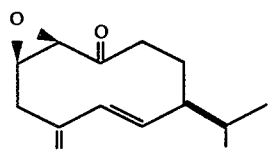

Xb beta-epoxide i. reacting Xa and Xb with a base strong enough to deprotonate a ketone followed by reaction with a selenylizing agent to form the selenide:

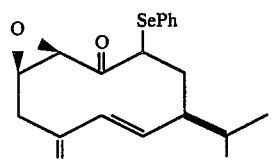

XI reacting XI with $H_2O_2$ to the corresponding selenoxide and rearranging the selenoxide in the presence of anhydrous sodium acetate and acetic anhydride to form the alpha-diketone:

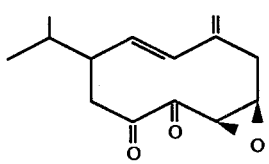

XII j. reacting XII with the ylide formed from trimethylsulfonium iodide and dimsyl sodium to form periplanone-B having the structure

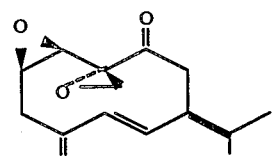

I

2. The process of claim 1, wherein the vinyl metallic halide used in (b) is vinyl magnesium bromide.

3. The process of claim 1, wherein the base used in (c) is the combination of 18-Crown-6 and KH.

4. The process of claim 1, wherein the base used in (f) and (i) is an amide base.

5. The process of claim 1, wherein the base used in (f) and (i) is lithium hexamethylidisilazide.

6. The process of claim 1, wherein the sulfenylating agent used in step (f) is benzenesulfonate-S-phenyl ester.

7. The process of claim 1, wherein the selenylizing agent used in step (i) is PhSeBr.

8. A process for synthesizing periplanone-B comprising:

a. reacting allene and 4-isopropyl-2-cyclohexen-1-one by photocycloaddition to form a mixture of:

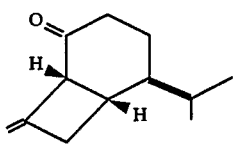

IIIa and

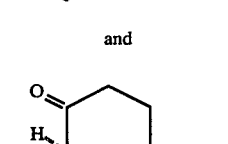

IIIb b. reacting the mixture of IIIa and IIIb with a vinyl metallic halide to form the corresponding allylic carbinols having the structure:

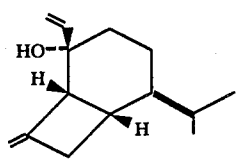

IVa and

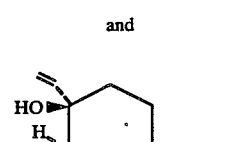

IVb c. reacting the product of step b with a base, wherein said base is a combination of 18-crown-6 and KH to form compounds having the structure:

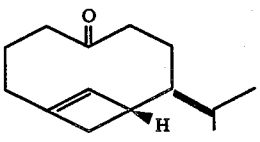

Va and

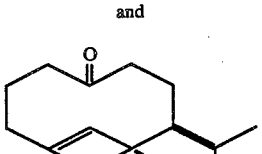

Vb d. heating the product of step c to thereby obtain electrocyclic ring opening to form a mixture of:

[Structures VI and VII shown]

in a molar ratio of cis-diene (VI) to trans-diene (VII) of about 2/1;

e. irradiating with light the mixture produced in step d to form a mixture of VI and VII in a molar rato of 1/15, respectively and isolating VII from such mixture;

f. reacting VII with lithium hexamethydisilazide followed by reaction with benzenesulfonate-S-phenyl ester ro form a 16/1 regioisomeric mixture of monosulfenylated ketones having the general formula:

[Structure VIII shown]

g. reacting the product of step f with NaIO$_4$ to form the corresponding sulfoxides followed by pyrolysis to form:

[Structure IX shown]

and isolating IX from the reaction mixture;

h. reacting IX with t-butyl hydroperoxide to form a mixture of cis epoxides Xa and Xb in a molar ratio of beta/alpha of about 4/1

[Structures Xa (alpha-epoxide) and Xb (beta-epoxide) shown]

i. reacting Xa and Xb with lithium hexamethyldisilazide followed by reaction with PhSeBr to form the selenide:

[Structure XI shown]

reacting XI with H$_2$O$_2$ to the corresponding selenoxide and rearranging the selenoxide in the presence of anhydrous sodium acetate and acetic anhydride to form the alpha diketone:

[Structure XII shown]

j. reacting XII with the ylide formed from trimethylsulfonium iodide and dimsyl sodium to form periplanone-B having the structure:

[Structure I shown]

* * * * *